US010997389B2

(12) United States Patent
Iwamoto et al.

(10) Patent No.: US 10,997,389 B2
(45) Date of Patent: May 4, 2021

(54) ELECTRONIC DEVICE WITH EXPOSED CONDUCTIVE MEMBER AT STEP IN MOLD AND FINGERPRINT RECOGNITION APPARATUS EQUIPPED WITH THE SAME

(71) Applicant: Murata Manufacturing Co., Ltd., Nagaokakyo (JP)

(72) Inventors: Takashi Iwamoto, Nagaokakyo (JP); Takeshi Uchida, Nagaokakyo (JP)

(73) Assignee: MURATA MANUFACTURING CO., LTD., Nagaokakyo (JP)

(*) Notice: Subject to any disclaimer, the term of this patent is extended or adjusted under 35 U.S.C. 154(b) by 0 days.

(21) Appl. No.: 17/062,864

(22) Filed: Oct. 5, 2020

(65) Prior Publication Data

US 2021/0019490 A1    Jan. 21, 2021

Related U.S. Application Data

(63) Continuation of application No. PCT/JP2019/007780, filed on Feb. 28, 2019.

(30) Foreign Application Priority Data

May 1, 2018    (JP) .............................. JP2018-088117

(51) Int. Cl.
*G06K 9/00*    (2006.01)
*H01L 23/31*    (2006.01)
(Continued)

(52) U.S. Cl.
CPC ....... *G06K 9/0002* (2013.01); *G06K 9/00053* (2013.01); *H01L 23/3121* (2013.01);
(Continued)

(58) Field of Classification Search
CPC .............. G06K 9/0002; G06K 9/00053; H01L 23/5387; H01L 23/485; H01L 23/5383; H01L 23/3121; H01L 23/5225
See application file for complete search history.

(56) References Cited

U.S. PATENT DOCUMENTS 6,551,248 B2    4/2003    Miller
7,192,798 B2 *  3/2007    Okada .................. G06K 9/0002
                                              257/680
(Continued)

FOREIGN PATENT DOCUMENTS

JP    2003235830 A    8/2003
JP    2004056504 A    2/2004
(Continued)

OTHER PUBLICATIONS

International Search Report issued for PCT/JP2019/007780, dated May 28, 2019.
(Continued)

*Primary Examiner* — John P. Dulka
(74) *Attorney, Agent, or Firm* — Arent Fox LLP

(57) ABSTRACT

An electronic device includes a first substrate having a wiring trace, a second substrate having an external terminal, a first electronic component disposed on a first surface of the first substrate, a second electronic component electrically connected to the first electronic component and disposed on a second surface of the first substrate, a mold layer encapsulating the first electronic component, and a conductive member disposed in the mold layer. The conductive member electrically connects the first substrate to the second substrate. A step is formed at an end of the mold layer, and the conductive member is exposed at the step. A distance between the first substrate and the second substrate is smaller than a distance between the first surface of the first
(Continued)

substrate and a surface of the first electronic component that is positioned opposite to the first substrate.

20 Claims, 4 Drawing Sheets

(51) Int. Cl.
  *H01L 23/538* (2006.01)
  *H01L 23/522* (2006.01)
  *H01L 23/485* (2006.01)
(52) U.S. Cl.
  CPC ........ *H01L 23/485* (2013.01); *H01L 23/5225* (2013.01); *H01L 23/5383* (2013.01); *H01L 23/5387* (2013.01)

(56) References Cited

U.S. PATENT DOCUMENTS

| | | | |
|---|---|---|---|
| 7,424,136 B2* | 9/2008 | Setlak | G06K 9/00053 |
| | | | 257/414 |
| 8,736,001 B2 | 5/2014 | Salatino et al. | |
| 8,888,004 B2 | 11/2014 | Setlak et al. | |
| 9,263,315 B2* | 2/2016 | Oda | H01L 33/56 |
| 9,443,126 B2* | 9/2016 | Kim | G06K 9/00053 |
| 9,613,249 B2 | 4/2017 | Salatino et al. | |
| 9,691,708 B1* | 6/2017 | Huang | H01L 23/5389 |
| 9,960,512 B2 | 5/2018 | Kato | |
| 10,055,631 B1* | 8/2018 | Wen | H01L 23/5389 |
| 10,229,306 B2* | 3/2019 | Kim | G06F 3/03547 |
| 10,672,972 B2 | 6/2020 | Motoki et al. | |
| 2003/0028108 A1 | 2/2003 | Miller | |
| 2003/0156743 A1* | 8/2003 | Okada | G06K 9/0002 |
| | | | 382/124 |
| 2006/0057756 A1* | 3/2006 | Sato | G06K 9/0002 |
| | | | 438/50 |
| 2009/0069689 A1 | 3/2009 | Isono | |
| 2011/0042812 A1* | 2/2011 | Kayukawa | H01L 24/73 |
| | | | 257/741 |
| 2011/0298711 A1* | 12/2011 | Dean | G06F 3/03545 |
| | | | 345/161 |
| 2011/0309482 A1 | 12/2011 | Salatino et al. | |
| 2012/0085822 A1* | 4/2012 | Setlak | G06K 9/605 |
| | | | 235/439 |
| 2013/0015743 A1* | 1/2013 | Tsai | B81B 3/0005 |
| | | | 310/300 |
| 2014/0205161 A1 | 7/2014 | Salatino et al. | |
| 2015/0380848 A1* | 12/2015 | Kato | H01R 12/78 |
| | | | 439/67 |
| 2016/0066429 A1* | 3/2016 | Taniguchi | H05K 1/0278 |
| | | | 361/749 |
| 2016/0254429 A1* | 9/2016 | Fujikawa | F21K 9/00 |
| | | | 257/88 |
| 2016/0350572 A1* | 12/2016 | Kim, | G06F 3/03547 |
| 2017/0229769 A1* | 8/2017 | Yokoyama | H01L 21/78 |
| 2017/0344872 A1* | 11/2017 | Komaki | H01L 21/56 |
| 2017/0357838 A1* | 12/2017 | Chen | G06K 9/00 |
| 2018/0040805 A1 | 2/2018 | Motoki et al. | |
| 2018/0108618 A1* | 4/2018 | Yamamoto | C23C 14/24 |
| 2018/0343332 A1* | 11/2018 | Kim | H04M 1/0249 |
| 2020/0043835 A1* | 2/2020 | Nomura | H01L 23/3121 |
| 2020/0183465 A1* | 6/2020 | Yoo | H01Q 1/2266 |
| 2020/0243453 A1* | 7/2020 | Wang | H01L 24/20 |
| 2020/0258839 A1* | 8/2020 | Aleksov | H01L 23/498 |
| 2020/0267479 A1* | 8/2020 | Chang | H01L 23/5385 |
| 2020/0281102 A1* | 9/2020 | Otsubo | H05K 3/28 |
| 2020/0328143 A1* | 10/2020 | Marinov | H01P 5/04 |

FOREIGN PATENT DOCUMENTS

| | | |
|---|---|---|
| JP | 2005507581 A | 3/2005 |
| JP | 2005242841 A | 9/2005 |
| JP | 2009061112 A | 3/2009 |
| JP | 2013534008 A | 8/2013 |
| JP | 2013541773 A | 11/2013 |
| JP | 2016048723 A | 4/2016 |
| JP | 2016163132 A | 9/2016 |
| JP | 2017511162 A | 4/2017 |
| WO | 2014185194 A1 | 11/2014 |

OTHER PUBLICATIONS

Written Opinion of the International Searching Authority issued for PCT/JP2019/007780, dated May 28, 2019.

* cited by examiner

ELECTRONIC DEVICE WITH EXPOSED CONDUCTIVE MEMBER AT STEP IN MOLD AND FINGERPRINT RECOGNITION APPARATUS EQUIPPED WITH THE SAME

CROSS REFERENCE TO RELATED APPLICATIONS

The present application is a continuation of PCT/JP2019/007780, filed Feb. 28, 2019, which claims priority to Japanese Patent Application No. 2018-088117, filed May 1, 2018, the entire contents of each of which are incorporated herein by reference.

TECHNICAL FIELD

The present disclosure relates to an electronic device and a fingerprint recognition apparatus equipped with the electronic device, and more particularly, to a technique to reduce the height of the electronic device that serves as a sensor for the fingerprint recognition apparatus.

BACKGROUND

In recent years, fingerprint recognition apparatuses used for performing personal identification have come into wide use for enhancing security. A fingerprint recognition apparatuses is used in various ways, for example, as an electronic key disposed at an entrance of a building, as used with an automatic telling machine (ATM), or as used in a portable electronic appliance, such as a mobile phone or a smartphone.

Japanese Unexamined Patent Application Publication (Translation of PCT Application) No. 2017-511162 (hereinafter referred to as "Patent Document 1") discloses an electronic device to be used for a fingerprint recognition apparatus. The electronic device disclosed in Patent Document 1 includes a sensor electrode for detecting fingerprints, an integrated circuit electrically connected to the sensor electrode, a first circuit substrate that is positioned above the integrated circuit and on which the sensor electrode is mounted, a second circuit substrate that is positioned below the integrated circuit and electrically connected to the first circuit substrate, a molding layer for protecting the integrated circuit, and a connection portion that electrically connects the first circuit substrate and the second circuit substrate.

In general, size and thickness reduction is highly demanded for portable electronic appliances, which necessitates size and thickness reduction of fingerprint recognition apparatuses to be used for the portable electronic appliances.

The electronic device for the fingerprint recognition apparatus disclosed in Patent Document 1, however, is configured such that the second circuit substrate is disposed below the integrated circuit. Reducing the height of the device may face difficulties due to the second circuit substrate interfering with the integrated circuit. In other words, the idiosyncratic feature of the electronic device for the fingerprint recognition apparatus disclosed in Patent Document 1 may pose difficulties in reducing the height of the device.

SUMMARY OF THE INVENTION

Accordingly, it is an object of the present disclosure to reduce the height of an electronic device to be used for a fingerprint recognition apparatus.

According to an exemplary aspect, an electronic device is provided that includes a first substrate having a wiring trace formed therein, a first electronic component disposed on a first surface of the first substrate, and a second electronic component disposed on a second surface of the first substrate. The second surface is opposite to the first surface, and the second electronic component is electrically connected to the first electronic component through the wiring trace. Moreover, the electronic device also includes a mold layer encapsulating the first electronic component, and a second substrate in which an external terminal is formed. The electronic device further includes a conductive member disposed in the mold layer and electrically connecting the first substrate and the second substrate to each other. A step (or step portion) is formed at an end of the mold layer, and the conductive member is exposed at the step. Moreover, the second substrate is disposed at the step. In a thickness direction of the first substrate, a distance between the first substrate and the second substrate is smaller than a distance between the first surface of the first substrate and a surface of the first electronic component that is positioned opposite to the first substrate.

According to another exemplary aspect, a fingerprint recognition apparatus is equipped with the above-described electronic device.

The electronic device according to the present disclosure is configured such that the second substrate is disposed at the step formed at the end of the mold layer, and in the thickness direction of the first substrate, the distance between the first substrate and the second substrate is smaller than the distance between the first surface of the first substrate and the surface of the first electronic component that is positioned opposite to the first substrate. With this configuration, the entire second substrate does not protrude from the mold layer, which suppresses an increase in the total thickness of the electronic device caused by the presence of the second substrate. Thus, the height of the electronic device can be reduced.

DETAILED DESCRIPTION OF EMBODIMENTS

Figure 1:
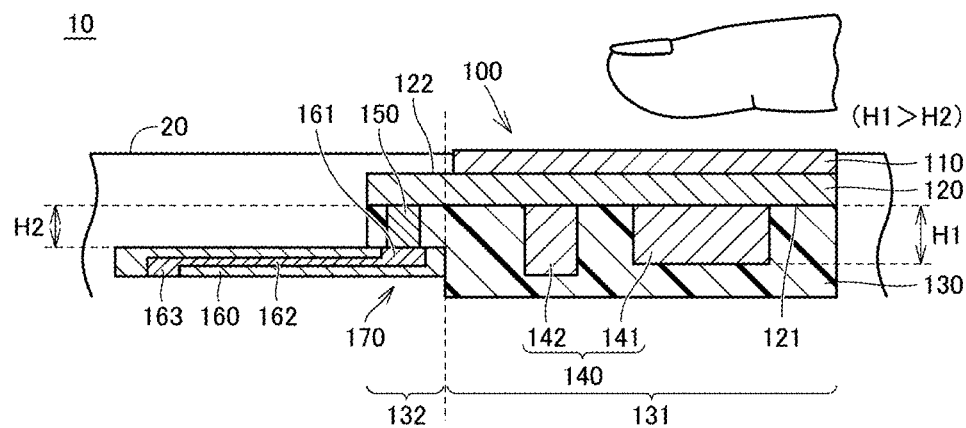
FIG. 1 is a cross-sectional view illustrating an electronic device according to an exemplary embodiment, which is included in a fingerprint recognition apparatus.

Exemplary embodiments and aspects of the present disclosure will be described in detail with reference to the drawings. It is noted that the same or similar elements in the drawings are denoted by the same reference signs, and repetitive explanation will be omitted.

FIG. 1 is a cross-sectional view illustrating an electronic device 100 according to an exemplary embodiment, which is included in a fingerprint recognition apparatus 10. The fingerprint recognition apparatus 10 is used, for example, as part of a portable electronic appliance, such as a smartphone.

As illustrated in FIG. 1, the electronic device 100 includes a sensor substrate 110 in which a sensor for detecting fingerprints is formed, a wiring substrate 120, an integrated circuit 141 for driving the sensor, a capacitor 142, a conductive member 150, a mold layer 130, and a terminal substrate 160. In an exemplary aspect, the electronic device 100 can be mounted in a portable electronic appliance in such a manner that the sensor substrate 110 is exposed from a housing 20 of the portable electronic appliance.

For example, an ultrasonic sensor is formed on the sensor substrate 110. When a user places a finger on the surface of the sensor substrate 110, an electric signal corresponding to irregularities of the fingerprint is generated. The electric signal generated in the sensor substrate 110 is transmitted to another device through wiring traces (not illustrated) formed by patterning in the wiring substrate 120 and also through the conductive member 150 and the terminal substrate 160.

The integrated circuit 141 and the capacitor 142 for noise reduction are disposed on a first surface 121 of the wiring substrate 120. The sensor substrate 110 is disposed on a second surface 122 of the wiring substrate 120 that is opposite the first surface 121. The wiring substrate 120 has a multilayer structure in which wiring traces are formed by patterning. The integrated circuit 141 and the capacitor 142 are electrically connected to the sensor substrate 110 by the wiring traces formed in the wiring substrate 120.

The mold layer 130 is made, for example, of a resin. The mold layer 130 encapsulates the integrated circuit 141 and the capacitor 142 on the first surface 121 of the wiring substrate 120. A step 170 (also referred to as a "step port") where the resin layer is made thin is formed at an edge of the mold layer 130. It is also noted that a thick part of the mold layer 130 is referred to as a "thick mold portion 131", while a thin part of the mold layer 130 at which the step portion 170 is formed is referred to as a "thin mold portion 132". The conductive member 150 is formed in the thin mold portion 132 so as to penetrate the mold layer 130 and be electrically connected to the wiring substrate 120. According to an exemplary aspect, the conductive member 150 is a columnar member made of an electrically conductive metal, such as copper, silver, gold, or aluminum. The conductive member 150 is exposed from the mold layer 130 at the step portion 170. It is noted that in the following description, the integrated circuit 141 and the capacitor 142 may be collectively referred to as "built-in components 140".

The terminal substrate 160 is a connector that transmits electric signals generated in the sensor substrate 110 to other devices (not illustrated). The terminal substrate 160 is a flexible circuit substrate preferably made of flexible materials. The dielectric substance of the terminal substrate 160 is, for example, a resin, such as an epoxy resin or a polyimide resin. Alternatively, the dielectric substance of the terminal substrate 160 may be a liquid crystal polymer (LCP) or a fluoro-resin. The terminal substrate 160 may be formed of a thermoplastic rigid circuit substrate.

As further shown, the terminal substrate 160 includes a terminal 161 exposed at one end of the terminal substrate 160, an external terminal 163 exposed at the other end thereof, and wiring traces 162. The wiring traces 162 are formed in the substrate and connect the terminal 161 to the external terminal 163 electrically. The terminal substrate 160 is disposed at the step portion 170 of the mold layer 130, and the terminal 161 is connected electrically to the conductive member 150.

A thickness H2 of the thin mold portion 132 at which the step portion 170 is formed (in other words, a distance in the thickness or vertical direction between the wiring substrate 120 and the terminal substrate 160) is smaller than the smallest distance H1 between the first surface 121 of the wiring substrate 120 and surfaces of the built-in components 140 that are the surfaces positioned opposite to the wiring substrate 120 (i.e., facing away from wiring substrate 120). With this configuration, the entire terminal substrate 160 does not protrude from the mold layer 130, which suppresses an increase in the total thickness of the electronic device 100 caused by the presence of the terminal substrate 160. Thus, the height of the electronic device 100 can be reduced compared with conventional designs.

Figure 2:
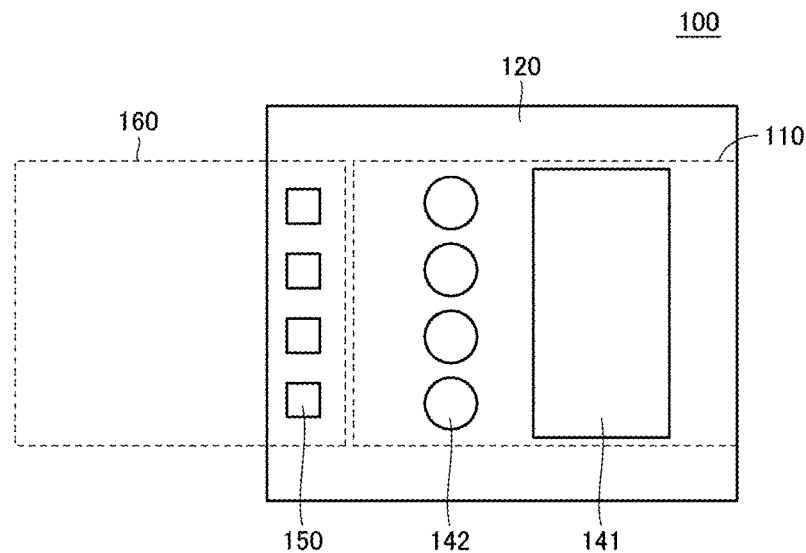
FIG. 2 is a plan view illustrating the electronic device.

FIG. 2 is a plan view illustrating the electronic device 100 when the first surface 121 of the wiring substrate 120 is viewed. It is noted that in FIG. 2, the resin of the mold layer 130 is omitted, thereby exposing conductive members 150 and the built-in components 140 disposed on the wiring substrate 120. In FIG. 2, the sensor substrate 110 and the terminal substrate 160 are indicated by the dotted lines. The sensor substrate 110 is disposed on the second surface 122 of the wiring substrate 120, and the terminal substrate 160 is to be attached to the step portion 170 of the mold layer 130.

As illustrated in FIG. 2, the sensor substrate 110 is disposed so as not to overlap the step portion 170. In other words, the sensor substrate 110 and the terminal substrate 160 do not overlap each other as viewed in plan in a direction normal to the electronic device 100 (e.g., normal to first surface 121), in other words. In the fingerprint recognition apparatus 10, a force is applied to the sensor substrate 110 in the thickness direction due to a user placing a finger on the sensor substrate 110, as described above. Since the sensor substrate 110 and the terminal substrate 160 are disposed so as not to overlap each other, the force applied to the sensor substrate 110 is prevented from affecting the terminal substrate 160.

FIGS. 3(a) to 3(f) are views illustrating an example process of manufacturing the electronic device 100. With reference to these figures, the conductive member 150 and the built-in components 140, such as the integrated circuit 141 and the capacitor 142, are first arrayed on a support base 50 by using a mounter (FIG. 3(a)). Next, the mold layer 130 is molded and solidified so as to cover the built-in components 140 and the conductive member 150 with an insulating sealing resin (FIG. 3(b)).

It is preferable that the sealing resin material be a low hygroscopicity material, such as an epoxy resin. Using the low hydroscopicity resin material can suppress corrosion at connection portions and deterioration of insulating films of the components encapsulated in the mold, which can improve the reliability of the electronic device. It is also preferable that the sealing resin material have a coefficient of linear expansion close to that of the built-in components encapsulated in the mold layer 130. Using the sealing resin material having a similar coefficient of linear expansion reduces thermal stress generated due to the difference of the coefficient of linear expansion caused by a temperature change. This can suppress breakage of the electronic device 100 due to strains or clacks.

Figure 3A:
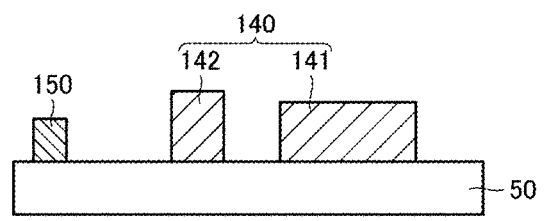
FIGS. 3(a) to 3(f) are views illustrating an exemplary process of manufacturing the electronic device.
Figure 3B:
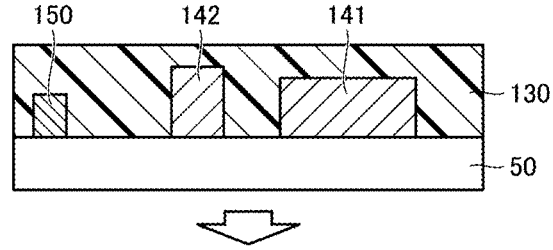
Figure 3C:
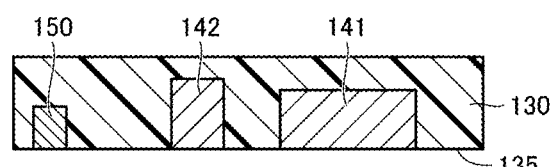
Figure 3D:
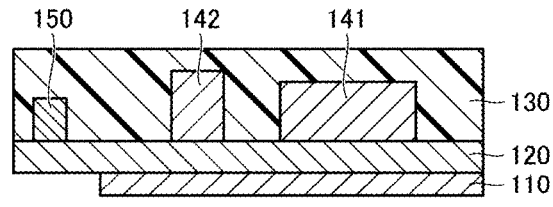

The support base 50 is removed after the mold layer 130 is formed (FIG. 3(c)). Subsequently, the wiring substrate 120 is formed in such a manner that insulating layers and metallic wiring layers having the wiring traces formed therein are laminated alternately onto a backside surface 135 of the mold layer 130 at which the built-in components are exposed (FIG. 3(d)). The metallic wiring layers are formed, for example, using the semi-additive process. The insulating layers are formed using photosensitive organic films. The height of the wiring substrate 120 can be reduced by laminating the metallic wiring layers and the insulating layers each of which has a thickness of approximately several micrometers. In the wiring substrate 120, the wiring traces formed in different metallic wiring layers are electrically connected through vias formed in the insulating layers.

After the wiring substrate 120 is formed, the sensor substrate 110 is disposed on the wiring substrate 120. Thus, the built-in components 140 in the mold layer 130 and the sensor substrate 110 are electrically connected by the wiring traces formed in the wiring substrate 120.

Figure 3E:
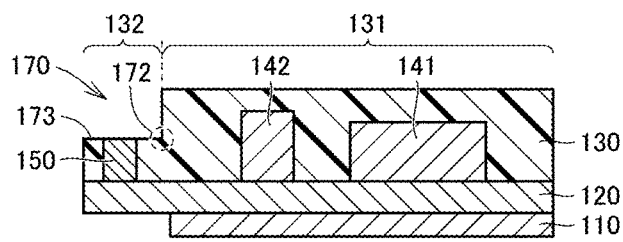

Next, the step 170 (i.e., step portion) is formed by cutting an end portion of the mold layer 130 halfway using a dicing machine, which exposes the conductive member 150 from the sealing resin material (FIG. 3(e)). Here, the mold layer 130 is cut off in such a manner that the height of an exposing surface 173 at which the conductive member 150 is exposed in the step portion 170 (in other words, the distance in the thickness direction between the wiring substrate 120 and the exposing surface 173) is made smaller than the height of any one of the built-in components 140 disposed on the wiring substrate 120.

In FIG. 3, the step portion 170 is formed in such a manner that the entire conductive member 150 is present within the thin mold portion 132 of the mold layer 130. Accordingly, a corner 172 in the step portion 170 is formed integrally of the resin of the mold layer 130. The corner 172 is susceptible to stress concentration. The corner 172, however, is not easier to break because the thick mold portion 131 and the thin mold portion 132 are integrally formed of the same material, compared with a case in which the thick mold portion 131 and the thin mold portion 132 are made as separate components. Encapsulating the conductive member 150 in resin molding can reinforce the wiring substrate 120 that has been formed as a multilayer body of thin films.

Figure 3F:
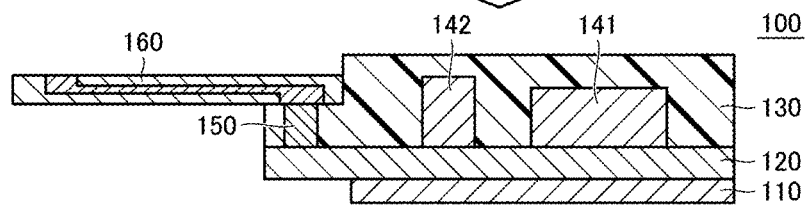

Finally, the electronic device 100 is produced by disposing the terminal substrate 160 at the step portion 170 (FIG. 3(f)). It should be appreciated that in FIG. 3(f), the electronic device 100 of FIG. 1 is illustrated upside down.

Figure 4:
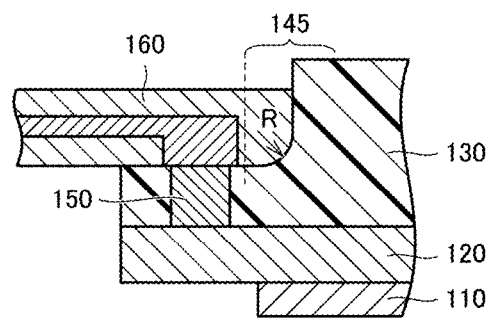
FIG. 4 is an enlarged cross-sectional view illustrating the vicinity of a step or step portion of the electronic device.

Regarding the corner 172 that is susceptible to stress concentration, the mold layer 130, and the terminal substrate 160 as well, may be rounded as illustrated in FIG. 4 so as to have a radius of curvature R at a boundary portion 145 that includes the boundary between the thick mold portion 131 and the thin mold portion 132, which thereby reduces the stress concentration.

It is also noted that the breakage of the corner 172 due to the stress concentration can be avoided using other configurations. First through third refinements of the exemplary aspects described below are examples in which the corner 172 is made of materials that are different from the sealing resin material.

Figure 5:
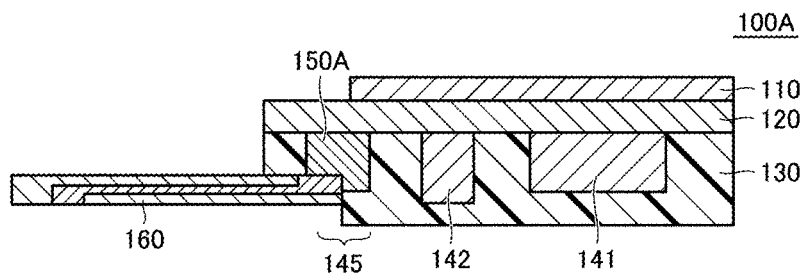
FIG. 5 is a cross-sectional view illustrating an electronic device of a first refinement of an exemplary aspect.

FIG. 5 is a cross-sectional view illustrating an electronic device 100A of a first refinement of an exemplary aspect. The electronic device 100A is configured such that a conductive member 150A that electrically connects the wiring substrate 120 to the terminal substrate 160 is disposed so as to extend across the boundary portion 145 that includes the boundary between the thick mold portion 131 and the thin mold portion 132 of the mold layer 130. In forming the step portion 170, part of the conductive member 150A is cut off in such a manner that the metallic material of the conductive member 150A is exposed at the corner 172. According to an exemplary aspect, the metallic material to be used for the conductive member 150A (for example, copper, silver, gold, or aluminum) typically has a strength greater than that of the resin material of the mold layer 130 and also has ductility, which is a typical characteristic of metal. This provides the corner 172 with a higher durability than the sealing resin material against stresses acting thereon.

Figure 6:
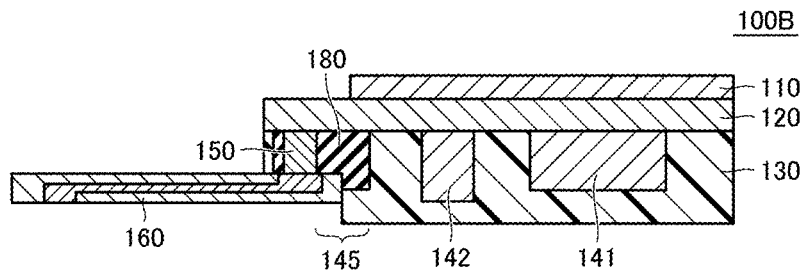
FIG. 6 is a cross-sectional view illustrating an electronic device of a second refinement of an exemplary aspect.

FIG. 6 is a cross-sectional view illustrating an electronic device 100B of a second refinement of an exemplary aspect. The electronic device 100B is configured such that a resin 180 having a modulus of elasticity greater than that of the sealing resin material of the mold layer 130 covers the conductive member 150 so as to extend across the boundary portion 145 of the mold layer 130. The resin 180 is exposed at the corner 172. The resin 180 has a greater rigidity than the sealing resin material of the mold layer 130 and thereby provides the corner 172 with a higher durability against the stresses acting thereon.

It is noted that the material having a high modulus of elasticity may be, for example, a resin mixed with an inorganic filler, such as silica or alumina.

Figure 7:
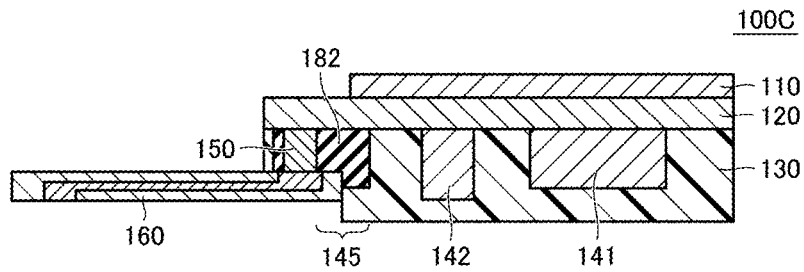
FIG. 7 is a cross-sectional view illustrating an electronic device of a third refinement of an exemplary aspect.

FIG. 7 is a cross-sectional view illustrating an electronic device 100C of a third refinement of an exemplary aspect. In contrast with the second refinement discussed above, the electronic device 100C is configured such that a resin 182 having a modulus of elasticity less than that of the sealing resin material of the mold layer 130 covers the conductive member 150 so as to extend across the boundary portion 145 of the mold layer 130. The resin 182 is exposed at the corner 172 and is more flexible and elastically deforms more easily compared with the sealing resin material of the mold layer 130. This reduces the likelihood of the corner 172 breaking because when stresses act on the corner 172, the resin 182 elastically deforms like a cushion and absorbs the stresses. This provides the corner 172 with a higher durability than the sealing resin material against the stresses acting thereon.

According to an exemplary aspect, the less elastic material may be, for example, a polyimide resin, a bismaleimide resin, a polyamide resin, a polyamide-imide resin, a polybenzoxazole resin, a benzocyclobutene resin, an aramid resin, a silicone resin, or a liquid crystal polymer.

It is noted that the configurations of the second and third refinements of exemplary aspects may be implemented by filling the resin 180 (or the resin 182) only partially so as to encapsulate the conductive member 150 before forming the mold layer 130 in the step in the manufacturing process illustrated in FIG. 3(b), and subsequently the entire mold layer 130 is formed using the sealing resin material.

Wiring Trace Arrangement in Wiring Substrate

In the case of an ultrasonic sensor being used as the sensor for fingerprint recognition, the arrangement of wiring traces in the wiring substrate 120 on which the sensor substrate 110 is disposed may influence the detection accuracy of the sensor.

Figure 8:
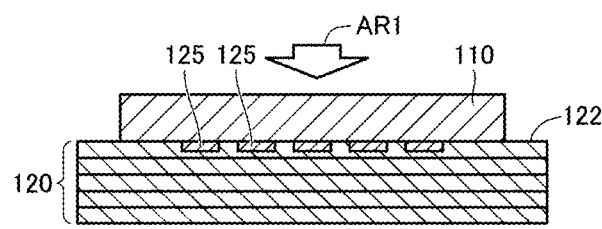
FIG. 8 is a view for explanation of a problem associated with arrangement of wiring traces in a wiring substrate.

The wiring traces made of a metallic material, such as copper, and the insulating layer made of a resin have different moduli of elasticity and different densities. The reflectivity of ultrasonic wave is also different. As illustrated in FIG. 8, in the case of the wiring traces being disposed on the second surface 122 of the wiring substrate 120, in other words, at a position immediately under the sensor substrate 110, when a user touches the sensor substrate 110 with a finger, a force is applied to the sensor substrate 110 in a direction AR1.

Here, uneven loads are applied to the sensor substrate 110 because wiring traces 125 have a density different from that of a resin portion without the wiring traces 125 at the contact surface between the sensor substrate 110 and the wiring substrate 120. This may cause the sensor substrate 110 to deform unevenly and thereby attenuate an ultrasonic wave unevenly at a detection surface of the sensor substrate 110.

Moreover, if the wiring traces 125 are disposed immediately under the sensor substrate 110, reflection of ultrasonic waves may become uneven between a portion at which each wiring trace 125 is in contact with the sensor substrate 110 and a portion at which the resin is in contact with the sensor substrate 110.

If the reflection of ultrasonic waves becomes different depending on presence or absence of the wiring trace 125 as described above, an image of the wiring traces 125 may be transferred onto an image of a detected fingerprint.

Figure 9:
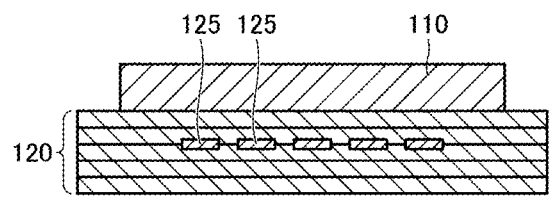
FIG. 9 is a view illustrating a first example of wiring trace arrangement in the wiring substrate.

Accordingly, in the wiring substrate 120, the wiring traces 125 are not basically disposed immediately under the sensor substrate 110 (i.e., on the second surface 122), and the wiring traces 125 are preferably not in contact with sensor substrate 110. In other words, as illustrated in FIG. 9, the wiring traces 125 are formed on an inner layer of the wiring substrate 120, and at least one insulating layer is interposed between the wiring traces 125 and the sensor substrate 110. With this configuration, ultrasonic waves are reflected evenly at the contact surface between the sensor substrate 110 and the wiring substrate 120, which can reduce the influence of the wiring traces 125 on a detection image produced by the ultrasonic sensor.

Figure 10:
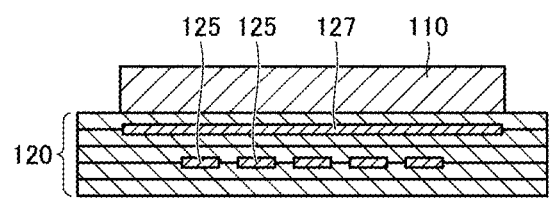
FIG. 10 is a view illustrating a second example of wiring trace arrangement in the wiring substrate.

It is also noted that depending on the type of resin to be used for the insulating layer, the detection image may be influenced considerably by the reflection at the wiring traces 125 even if the wiring traces 125 are formed on an inner layer of the wiring substrate 120. In such a case, as illustrated in FIG. 10, an intermediate layer 127 made of a metal or another insulating material may be disposed between the sensor substrate 110 and the wiring traces 125 so as to shield the wiring traces 125. The reflection of ultrasonic waves is thereby made uniform.

Figure 11:
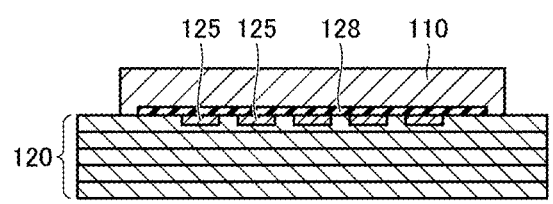
FIG. 11 is a view illustrating a third example of wiring trace arrangement in the wiring substrate.

As illustrated in FIG. 11, when it is necessary to form the wiring traces 125 on the second surface 122 of the wiring substrate 120, the wiring traces 125 may be covered with the intermediate layer 128 made of a metal or another insulating material, and the sensor substrate 110 may be disposed on the intermediate layer 128. This configuration can suppress uneven reflection of ultrasonic waves caused by the wiring traces 125 and can thereby make detection images of the ultrasonic sensor clearer.

REFERENCE SIGNS LIST 10 fingerprint recognition apparatus
20 housing
50 support base
100, 100A to 100C electronic device
110 sensor substrate
120 wiring substrate
121 first surface
122 second surface
125, 162 wiring traces
127, 128 intermediate layer
130 mold layer
131 thick mold portion
132 thin mold portion
135 backside surface
140 built-in component
141 integrated circuit
142 capacitor
145 boundary portion
150, 150A conductive member
160 terminal substrate
161, 163 terminal
170 step portion
172 corner
173 exposing surface
180, 182 resin

The invention claimed is:

1. An electronic device, comprising:
a first substrate having a wiring trace formed therein;
a first electronic component disposed on a first surface of the first substrate;
a second electronic component disposed on a second surface of the first substrate that is opposite to the first surface, with the second electronic component being electrically connected to the first electronic component by the wiring trace;
a mold layer encapsulating the first electronic component;
a second substrate having an external terminal formed thereon;
a conductive member disposed in the mold layer and electrically connecting the first substrate to the second substrate; and
a step disposed at an end of the mold layer, such that the conductive member is exposed at the step,
wherein the second substrate is disposed at the step, and
wherein, in a thickness direction of the first substrate, a distance between the first substrate and the second substrate is smaller than a distance between the first surface of the first substrate and a surface of the first electronic component that is opposite to the first substrate.

2. The electronic device according to claim 1, wherein the second substrate does not overlap the second electronic component when viewed in a plan view that is in a direction normal to the first surface of the first substrate.

3. The electronic device according to claim 1, wherein mold layer has a thin mold portion in the thickness direction that includes the step and a thick mold portion in the thickness direction that does not include the step.

4. The electronic device according to claim 3, wherein a region that includes a boundary between the thin mold portion and the thick mold portion integrally comprises a material of the mold layer.

5. The electronic device according to claim 3, wherein the conductive member is exposed at a region that includes a boundary between the thin mold portion and the thick mold portion.

6. The electronic device according to claim 3, further comprising a curved boundary between the thin mold portion and the thick mold portion.

7. The electronic device according to claim 3, wherein, when the electronic device is viewed in a plan view in a direction normal to the electronic device, the second electronic component is disposed within an area over which the thick mold portion extends.

8. The electronic device according to claim 1, further comprising a member formed from a material having a modulus of elasticity that is greater than a modulus of elasticity of a material of the mold layer, with the member disposed at a region that includes a boundary between the thin mold portion and the thick mold portion.

9. The electronic device according to claim 1, further comprising a member formed from a material having a modulus of elasticity that is smaller than a modulus of elasticity smaller of a material of the mold layer, with the member disposed at a region that includes a boundary between the thin mold portion and the thick mold portion.

10. The electronic device according to claim 1, wherein the second electronic component is an ultrasonic sensor that is not in contact with the wiring trace of the first substrate.

11. The electronic device according to claim 10, wherein the first substrate has a multilayer structure comprising a plurality of laminated insulating layers.

12. The electronic device according to claim 11, wherein at least one of the plurality of laminated insulating layers is disposed between the second electronic component and the wiring trace.

13. The electronic device according to claim 10, further comprising at least one insulating layer or a metallic layer disposed between the second electronic component and the first substrate.

14. The electronic device according to claim 1, wherein the second substrate is a flexible circuit substrate.

15. The electronic device according to claim 1, wherein the thickness direction of the first substrate is a direction normal to the first surface of the first substrate.

16. The electronic device according to claim 1, wherein the second electronic component is a touch sensor and the first electronic component is an integrated circuit configured to drive the touch sensor.

17. The electronic device according to claim 1, wherein the second substrate comprises a wiring trace that electrically connects the external terminal to the conductive member.

18. The electronic device according to claim 1, wherein a distance between the first surface of the first substrate and a surface of the second substrate that faces the first substrate is smaller than the distance between the first surface of the first substrate and the surface of the first electronic component that is opposite to the first substrate.

19. The electronic device according to claim 1, wherein a corner of the step is defined by the mold layer and is rounded to prevent stress concentration.

20. A fingerprint recognition apparatus, comprising the electronic device according to claim 1.

* * * * *